(12) United States Patent
Yoshida

(10) Patent No.: US 6,437,257 B1
(45) Date of Patent: Aug. 20, 2002

(54) WEIGHING MACHINE

(76) Inventor: Minoru Yoshida, 2-21-17-204, Negishi, Taito-ku, Tokyo 110-0003 (JP)

( * ) Notice: Subject to any disclaimer, the term of this patent is extended or adjusted under 35 U.S.C. 154(b) by 35 days.

(21) Appl. No.: 09/679,148

(22) Filed: Oct. 5, 2000

(30) Foreign Application Priority Data

Aug. 1, 2000 (JP) ........................................ 2000-232997

(51) Int. Cl.$^7$ ........................ G01G 19/00; A61B 5/103
(52) U.S. Cl. ........................ 177/199; 177/200; 600/587; 600/592
(58) Field of Search ................................ 177/199, 200; 600/587, 592

(56) References Cited

U.S. PATENT DOCUMENTS

| | | | | |
|---|---|---|---|---|
| 3,169,022 A | * | 2/1965 | Kretsinger | 177/200 |
| 3,616,690 A | * | 11/1971 | Harden | 177/200 |
| 4,014,398 A | * | 3/1977 | Gresko | 600/592 |
| 4,711,313 A | * | 12/1987 | Iida et al. | 177/199 |
| 5,414,225 A | * | 5/1995 | Garfinkle | 177/199 |

FOREIGN PATENT DOCUMENTS

| | | | | |
|---|---|---|---|---|
| JP | 55-141628 | * | 11/1980 | 600/587 |
| JP | 62-34016 | * | 2/1987 | 600/587 |

* cited by examiner

*Primary Examiner*—Randy W. Gibson
(74) *Attorney, Agent, or Firm*—Armstrong, Westerman & Hattori, LLP (57) ABSTRACT

A weighing machine useful for chiropractic and other medical treatment by accurately grasping the bias of the right and left, and front and rear weights of the person, and by recording momently changing center of the weight rested on right and left feet each, and center of the weight of the whole body. The weighing machine comprises two weighing device arranged right and left with a predetermined distance between them, and each weighing device is provided with a case body with a bottom plate, four weighing mechanisms arranged right and left, and back and forth on the bottom plate, means for positioning a person to be measured on the four weighing devices.

9 Claims, 16 Drawing Sheets

WEIGHING MACHINE

BACKGROUND OF THE INVENTION

1. Field of the Invention

The present invention relates to a weighing machine, and more particularly to a weighing machine used for general medical treatment including osteopathy and chiropractic.

2. Description of the Related Art

So far, as a part of health care, body weight has been used to check a person is health or not. For example, sick person, aged person and the like lose their balance of right and left sides of the body, so that it is necessary to easily check whether on right foot or on left foot more weight is rested, and so on, to cure the unstable balance.

Figure 14A:
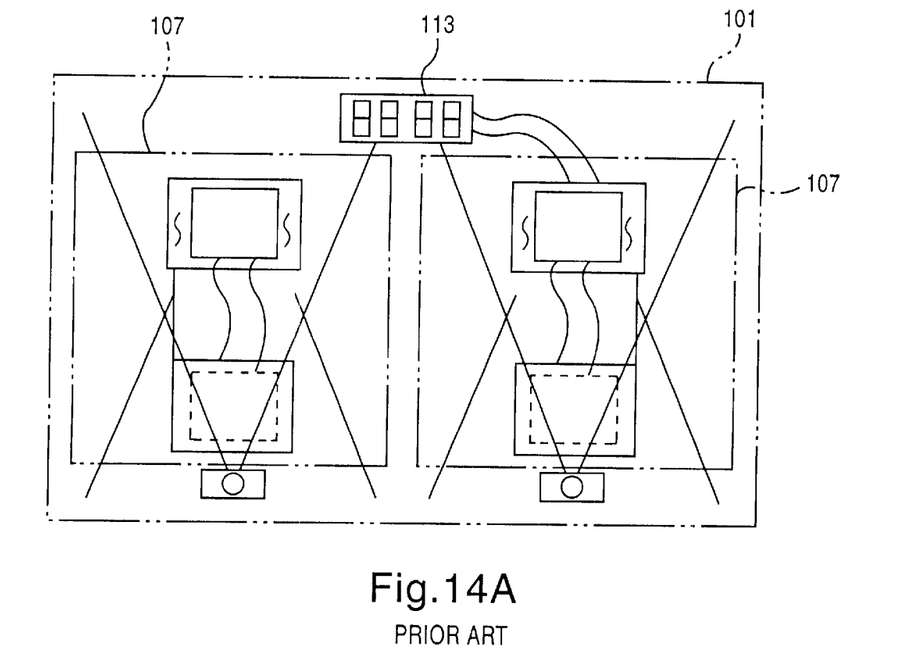
FIGS. 14A and 14B are a plan view and a front view respectively of a conventional weighing machine.
Figure 14B:
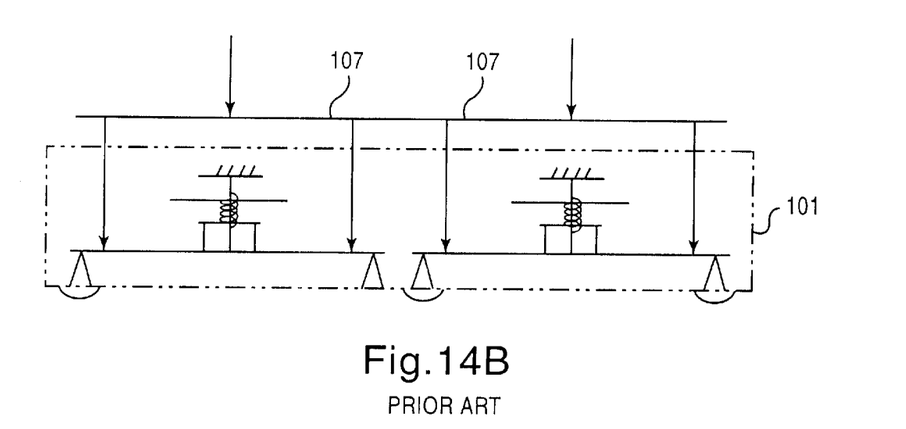

In order to measure the weights rested on right foot and left foot, a weighing machine illustrated in FIG. 14 is proposed in Japanese patent application laid open Showa 61-52236. This weighing machine digitally displays weight after converting to quantity of electricity through weighing mechanism. The weighing machine is provided with means for converting weight to quantity of electricity through weighing mechanism which is independently disposed in right and left sections of an base 101, and weight is rested on each step 107 of the measuring mechanism to display, for a predetermined period of time, the sum of the right and left weights and the difference between them.

Figure 15:
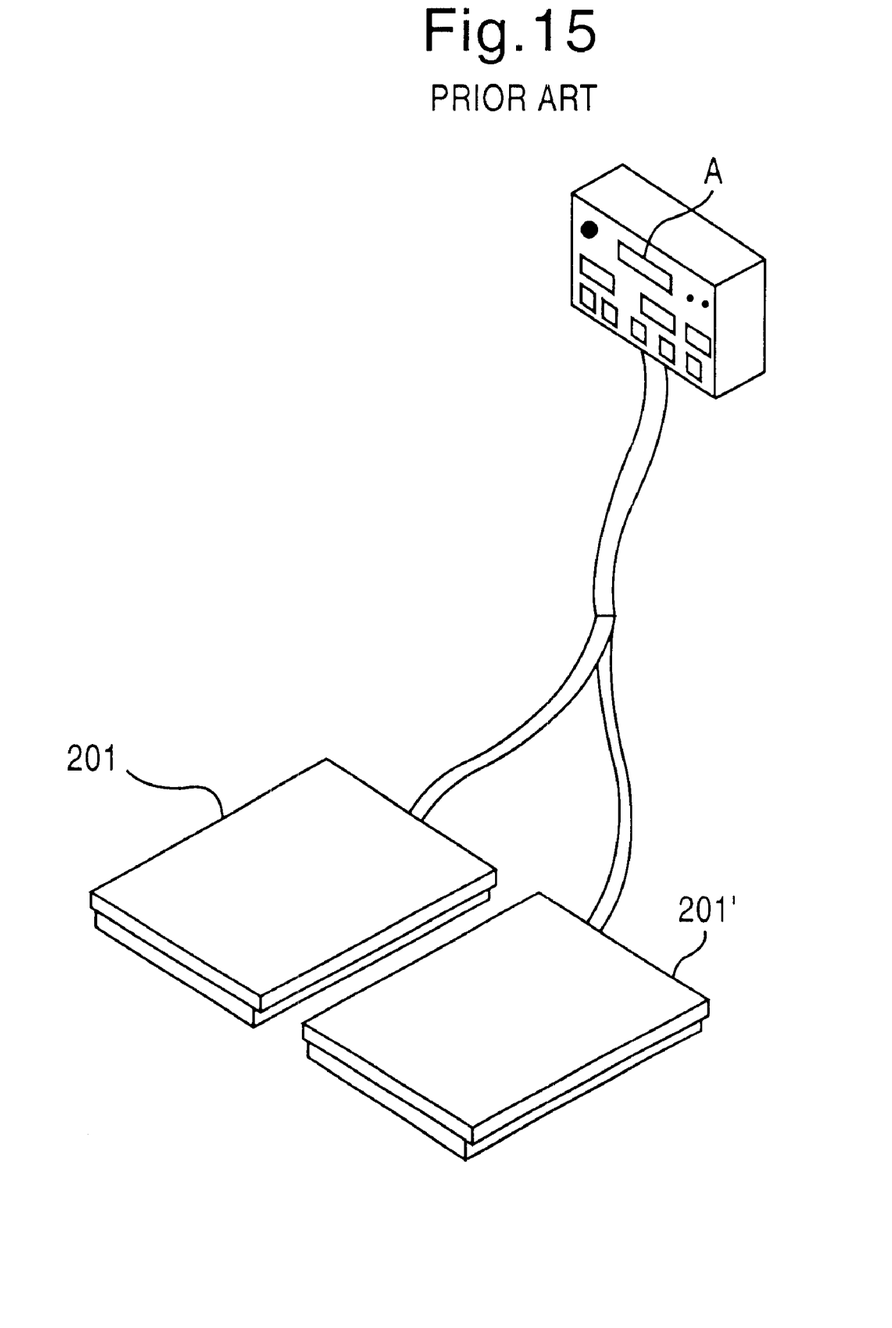
FIG. 15 is a schematic perspective view of another conventional weighing machine.

The weighing machine shown in FIG. 15, which is disclosed in Japanese patent application laid open Showa 62-273415, is also used for the same purpose, and is. This weighing machine simultaneously measures the weight of a person through more than one weighing devices 201, 201', and calculates the difference of the weights among the weighing devices. With this apparatus, weight is not displayed after a person starts the measurement by each weighing machine until measured values become stable, and at the moment the measured values are within a predetermined range the condition is notified to the person and the sum of the weights is displayed on a display section A. The data from the weighing devices are stored, and the differences of the weights among the weighing devices are divided into sections and displayed.

The first conventional weighing machine is provided with only two weighing mechanisms (right and left weighing mechanisms), therefore, only right and left balance of the weight of the body can be measured, but it is impossible to grasp front and rear balance of the weight of the body, which makes it difficult to use the data obtained for the purpose of osteopathy and chiropractic.

Further, in the second conventional apparatus, more than one weighing device is used, but no means for positioning the person is mounted, so that it is difficult to accurately grasp the right and left, and front and rear balances of the weight of the person.

To solve the above-mentioned problems, the present applicant invented a four-divided weighing machine, and the machine is registered as Japanese utility model registration No. 3022108.

Figure 16:
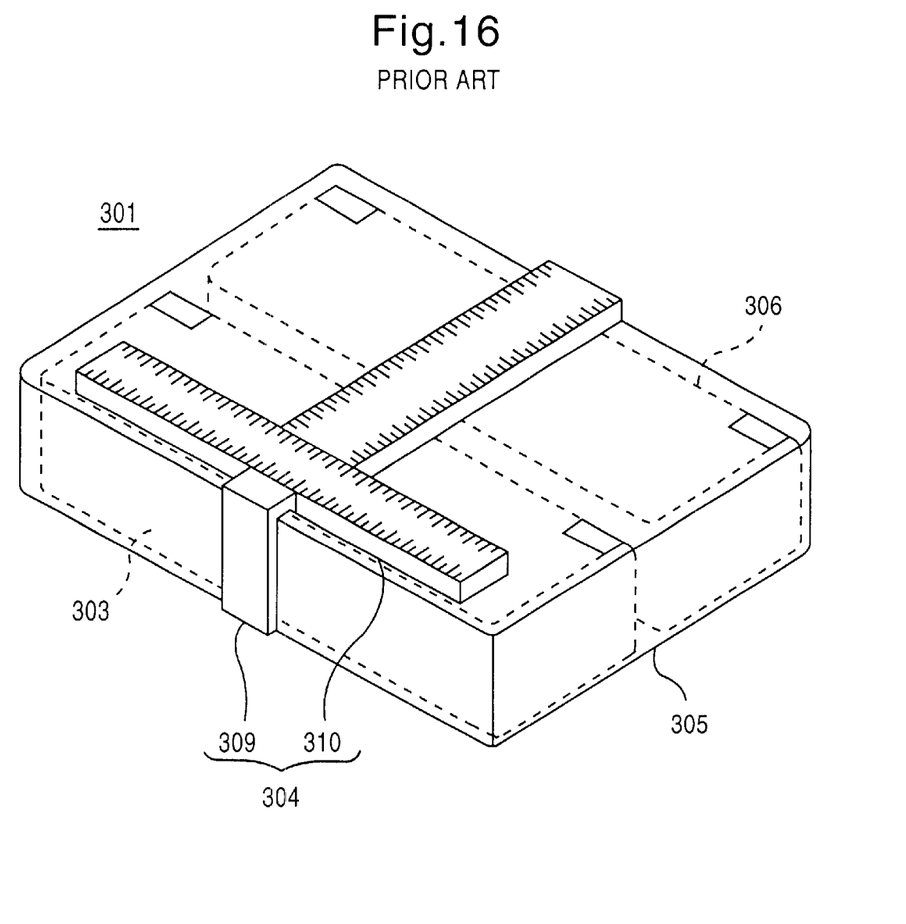
FIG. 16 is a schematic perspective view of a conventional four-divided weighing machine.

As illustrated in FIG. 16, this weighing machine 301 is simply constructed, and provided with a bottom plate 305, four weighing mechanisms 303 arranged right and left, and back and forth on the bottom plate 305, a step 306 mounted on the four weighing mechanisms 303, and means 304, which includes a slider holding portion 309 and a slider 310, for positioning the person standing on the step 306. The four weighing mechanisms 303 arranged right and left, and back and forth make it possible to accurately measure the bias of the right and left, and front and rear weights of the person, which provides sufficient data for general medical treatment including osteopathy and chiropractic.

This time, the present applicant modified the aforementioned weighing machine, and provides a new weighing machine that is more useful for chiropractic and other medical treatment by more accurately grasping the bias of the right and left, and front and rear weights of the person, and by recording momently changing center of the weight rested on right and left feet each, and center of the weight of the whole body.

SUMMARY OF THE INVENTION

To accomplish the above objective, the weighing machine according to the present invention comprises two weighing device arranged right and left with a predetermined distance between them, and each weighing device is provided with a case body with a bottom plate, four weighing mechanisms arranged right and left, and back and forth on the bottom plate, means for positioning a person to be measured on the four weighing devices.

With the above weighing machine according to the present invention, in addition to the bias of the weights rested on right and left feet of a person to be measured, it is possible to measure four-divided distribution of the weights rested on right and left feet respectively, the center of gravity of the weights, the center of gravity of whole body and so on, which provides remarkably useful data for chiropractic and other medical treatment.

In the above weighing machine according to the present invention, the positioning means may include channels formed between side walls of the four weighing mechanisms.

Further, it is possible to form the weighing machine described above such that each weighing device has a load cell, and the weighing machine is provided with weight measuring means for converting electrical voltage measure by the load cell to weight data, storing means for storing the weight data, processing means for processing the weight data stored in the storing means, and displaying means for displaying data processed by the processing means.

BRIEF DESCRIPTION OF THE DRAWINGS

The present invention will be more apparent from the ensuring description with reference to the accompanying drawings wherein.

DETAILED DESCRIPTION OF PREFERRED EMBODIMENTS

Now, preferred embodiments of the present invention will be explained with reference to drawings.

Figures 1A, 1B:
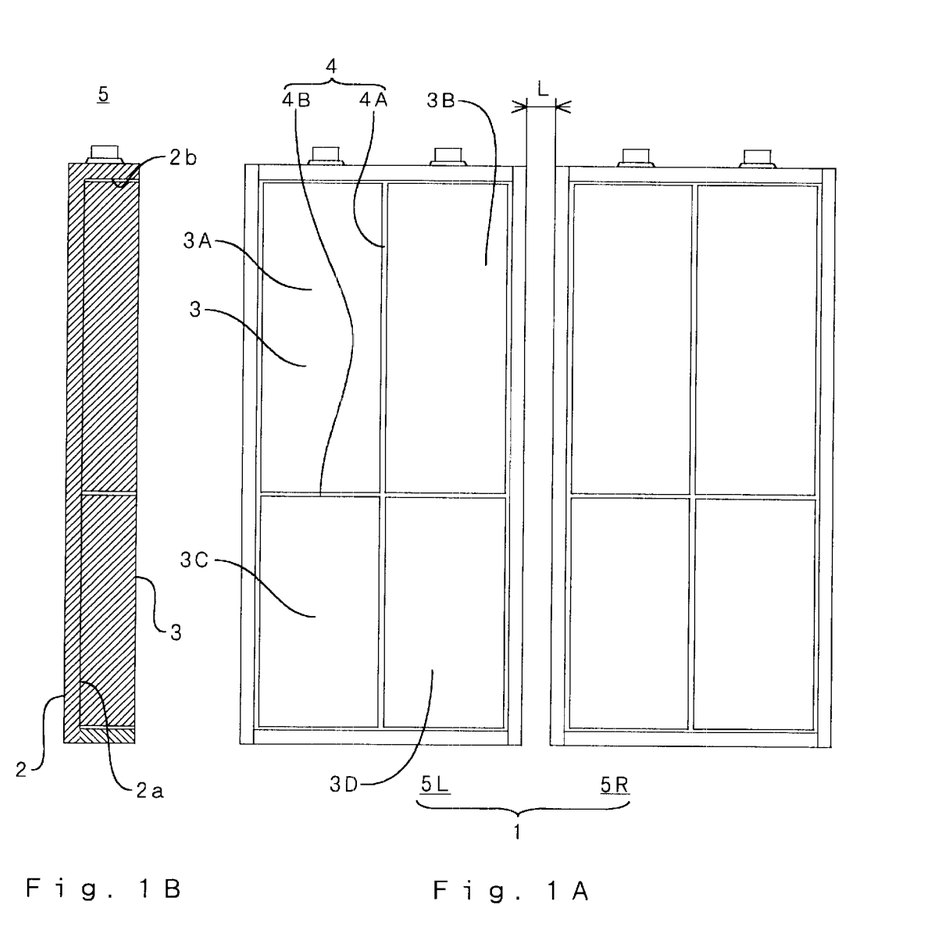
FIGS. 1A and 1B are a plan view and a side view respectively of a weighing machine according to one embodiment of the present invention.

FIGS. 1A and 1B show a weighing machine according to an embodiment of the present invention, and the weighing machine 1 comprises two weighing device 5 (5R, 5L) that are arranged right and left with a predetermined distance between them, and each weighing device is provided with a case body 2 with a bottom plate 2a, four weighing contiguous mechanisms 3 (3A arranged right and left, and back and forth on the bottom plate 2a, and channels 4 (4A, 4B), as means for positioning a person to be measured, which are formed between the side walls of the weighing mechanisms 3.

The case body 2 is made from synthetic resin, stainless steel, or the like so as to be a rectangular with longer left (or right) side compared with upside (or downside) when observed from the above, and four weighing mechanisms 3 are arranged on the bottom plate 2a and are enclosed by the side walls 2b.

The width of each weighing mechanism 3 that are disposed on the bottom plate 2a of the case body 2 are the same, but the length of the two weighing mechanisms 3A and 3B arranged forward are longer than those of the weighing mechanisms 3C and 3D arranged backward. This is because both medial malleolus lines decide the lengths. Each weighing mechanism 3 is provided with a load cell not shown which measures the weight rested on the weighing mechanism 3.

Two weighing devices 5 with the above-mentioned construction are disposed right and left with a predetermined distance between them. The distance L is determined by the height of the person measured. For example, when a person of 170 cm tall is measured, the distance L is set to be approximately 10 cm.

Figure 2:
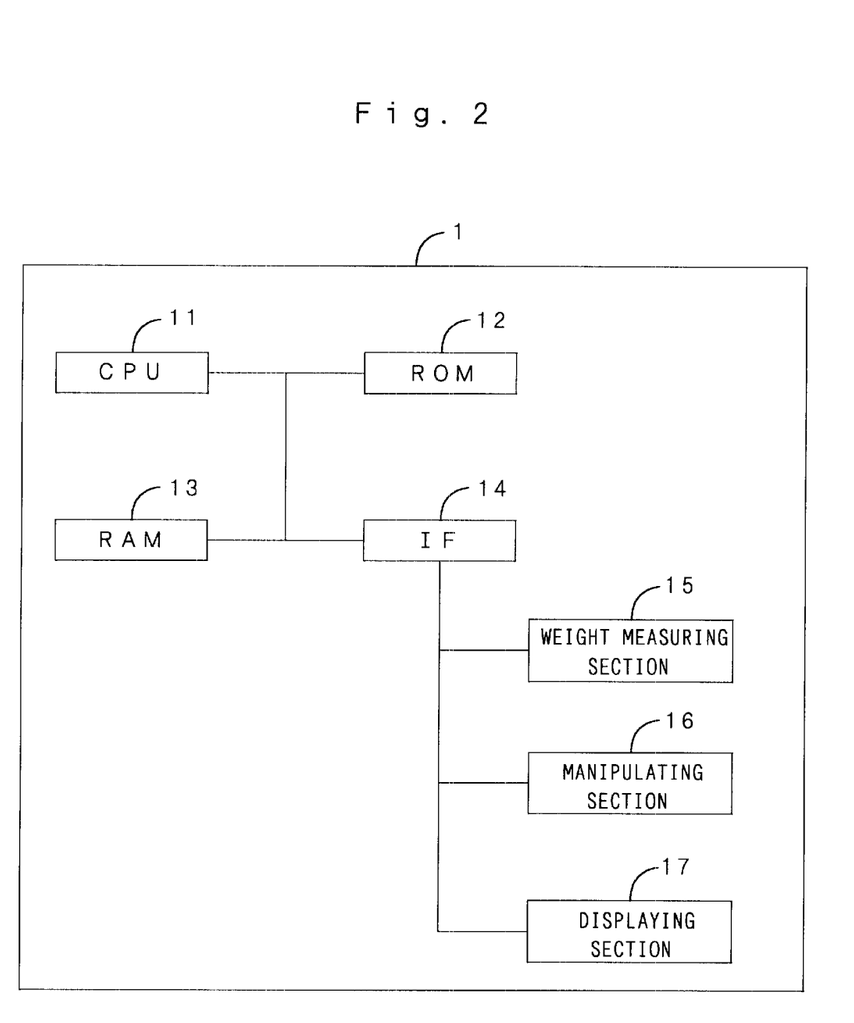
FIG. 2 is a block diagram showing electrical system of the weighing machine illustrated in FIG. 1.

Next, the electrical system of the weighing machine 1 will be explained with reference to FIG. 2.

This weighing machine 1 is provided with a CPU 11, a ROM 12, a RAM 13, an interface circuit (IF) 14, a weight measuring section 15, a manipulating section 16, and a displaying section 17. The CPU 11, the ROM 12, the RAM 13 and the IF 14 are connected with a bass to each other. A personal computer or the like may realize this system. To the IF 14 is connected the weight measuring section 15, the manipulating section 16, and the displaying section 17.

The CPU 11 controls the overall weighing machine 1 based on programs stored in the ROM 12. In the ROM 12 are stored data such as programs for activating the CPU 11. The RAM 13 stores data such as measured values by the weight measuring section 15, and the age and the distinction of sex of a person to be measured. Further, the IF 14 controls the communication between the CPU 11 and the weight measuring section 15, manipulating section 16, or displaying section 17.

The weight measuring section 15 includes a load cell, and measures the weight of the person riding on the weighing mechanism 3 to output electrical signal according to the measured value.

The displaying section 17 is, for instance, a CRT or the like which is attached to a personal computer, and is controlled by the CPU 11 to display the measured values from the weight measuring section 15 and data that are obtained by processing the measured values so as to be useful.

The manipulating section 16 is a keyboard or the like attached to a personal computer. An operator inputs necessary data through the manipulating section 16, and changes the content displayed on the displaying section 17, that is, the manipulating section 16 outputs signals in accordance with the operation by an operator.

With the above system, measured values from the weight measuring section 15 are stored in the RAM 13, and prescribed calculation is performed in the CPU 11 in accordance with operation signals that are inputted through the manipulating section 16, and the result is displayed on the displaying section 17 for medical treatment including osteopathy and chiropractic.

Next, the reason why the weighing device 5 is arranged right and left (totally two weighing device 5 are installed) with four weighing mechanisms 3 which are arranged right and left, and back and forth will be explained.

When only one weighing device is arranged back and forth respectively (totally two weighing machines are installed), as described above, only unbalance of right and left sides of a body is measured. This unbalance of right and left sides of the body provides data relating to eccentricity and inclination of the body. But, to utilize for osteopathy, chiropractic, and the like, data relating to the rotation of the body is further necessary, and to do so, the unbalance of front and rear weights of the body must be measured, so that the present applicant arranged four weighing mechanisms 303 in a case of the weighing machine registered in Japanese utility model registration No. 3022108.

In the present invention, in order to provide data more useful for chiropractic and other medical treatment, not only the unbalance of right and left, and front and rear weights rested on each foot is measured, but also momently changing center of the weight rested on right and left feet each, and center of the weight of the whole body are recorded by using four-divided weighing device that is arranged right and left.

Next, how to use the weighing machine 1 with the above construction will be explained.

Figure 3:
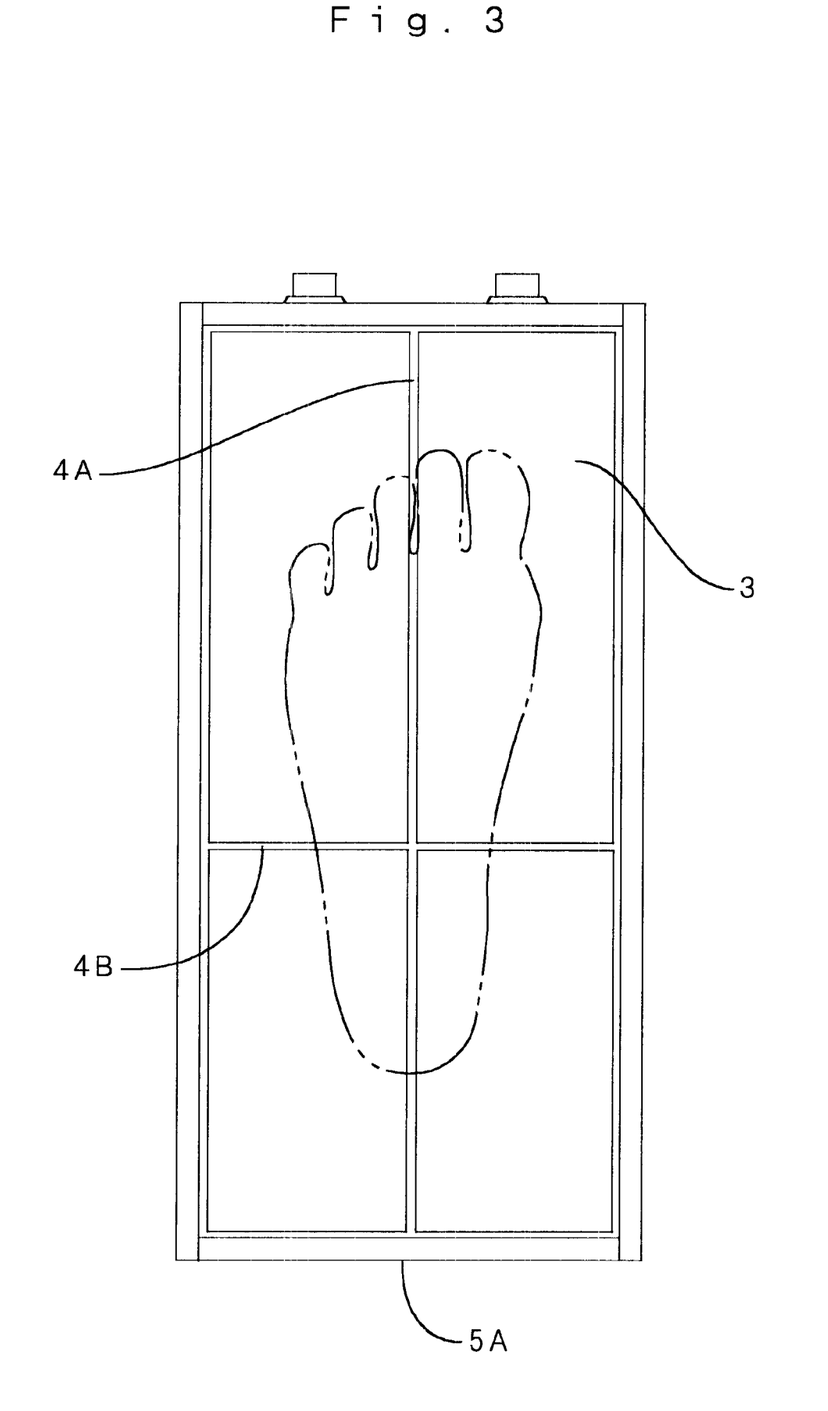
FIG. 3 is a drawing for explaining a method of positioning a person to be measured when using the weighing machine illustrated in FIG. 1.

Firstly, as illustrated in FIG. 3, a person to be measured puts a foot (left foot in the figure) in such a manner that the portion between the index finger and the middle finger, and the center of the Achilles' tendon coincides with a vertical positioning channel 4A, and the front edge of medial malleolus coincides with a lateral positioning channel 4B. Although an illustration is omitted, another foot (right foot) is to be positioned in the same manner.

Next, power is supplied to the weighing machine 1 to start the measurement. The measurement is performed for 120 seconds, and momently changing weights rested on the weighing mechanisms 3 are measured. Then, from the data, distributions of the weights on right and left feet, and whole body, and the transition of the center of gravity of the weights rested on right and left feet, and the transition of the center of gravity of whole body are calculated and graphically presented for analysis. The reason why the measurement continues for 120 seconds is that although the center of gravity of a person to be measured does not move very much after 30 seconds after measurement start since the person is in a state of nervous tension, after that, the person's tension is relieved and natural movement of the center of gravity can be measured.

Next, an example of medical treatment using the weighing machine according to the present invention will be explained.

Figure 4:
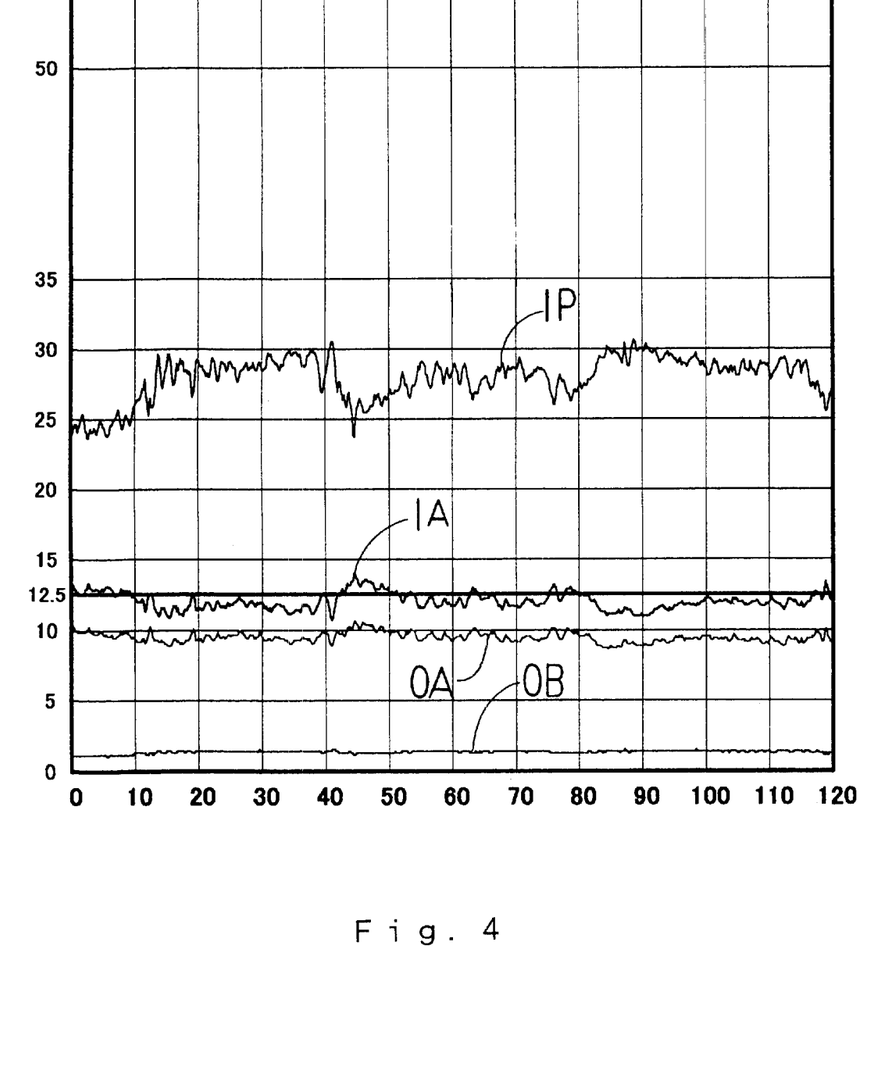
FIG. 4 is a graph showing four-divided weights of a patient rested on the left foot before medical treatment.
Figure 5:
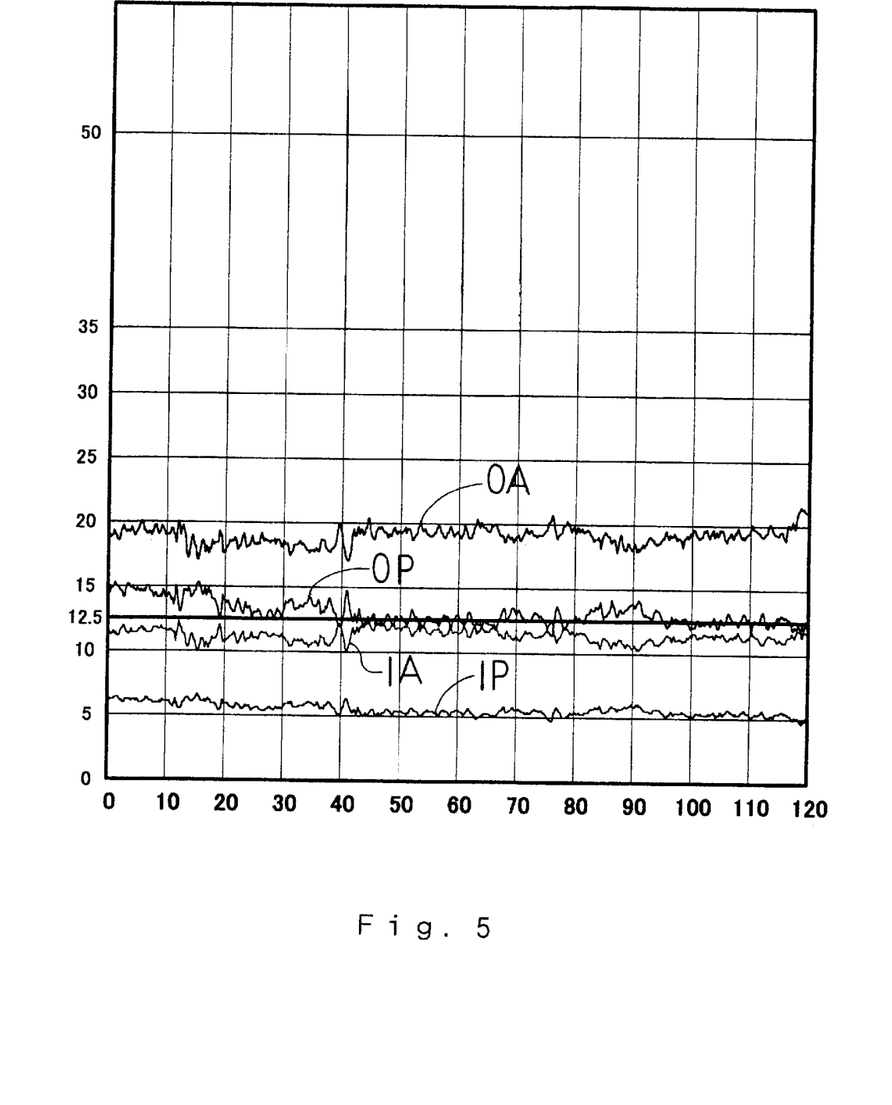
FIG. 5 is a graph showing four-divided weights of a patient rested on the right foot before medical treatment.

FIGS. 4 to 8 show the measurement result of the weight of a patient before medical treatment. FIGS. 4 and 5 are graphs showing the transition (for 120 seconds) of four-divided weight of the patient rested on the right and left feet respectively. In the figures, OA, OP, IA, and IP are percentages of the weights rested on outer forward, outer rearward, inner forward, and inner rearward weighing mechanism 3 respectively to the weight of the whole body.

Figure 6:
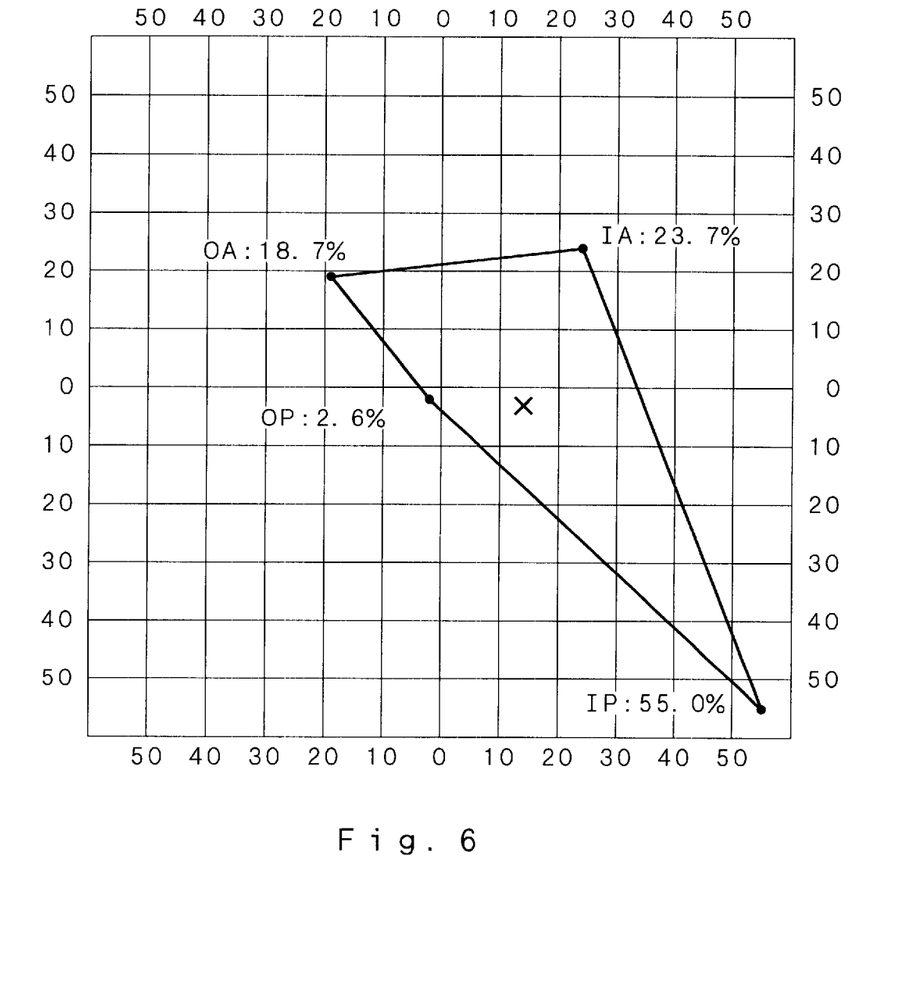
FIG. 6 is a graph showing mean values of four-divided weights of a patient rested on the left foot before medical treatment.
Figure 7:
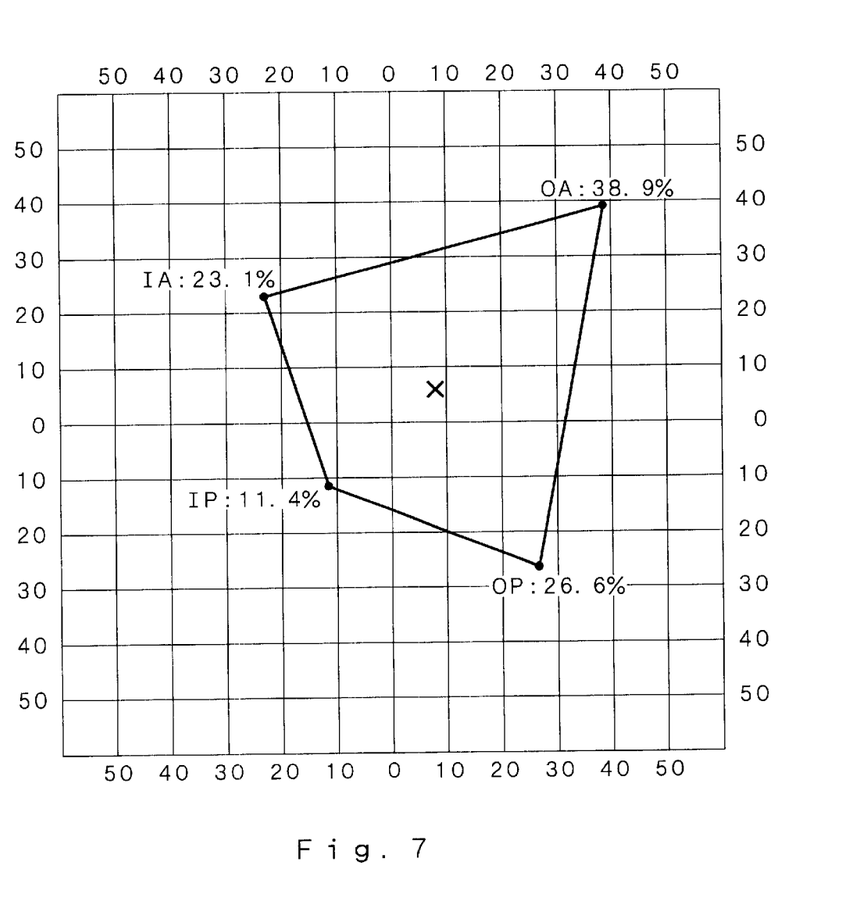
FIG. 7 is a graph showing mean values of four-divided weights of a patient rested on the right foot before medical treatment.
Figure 8:
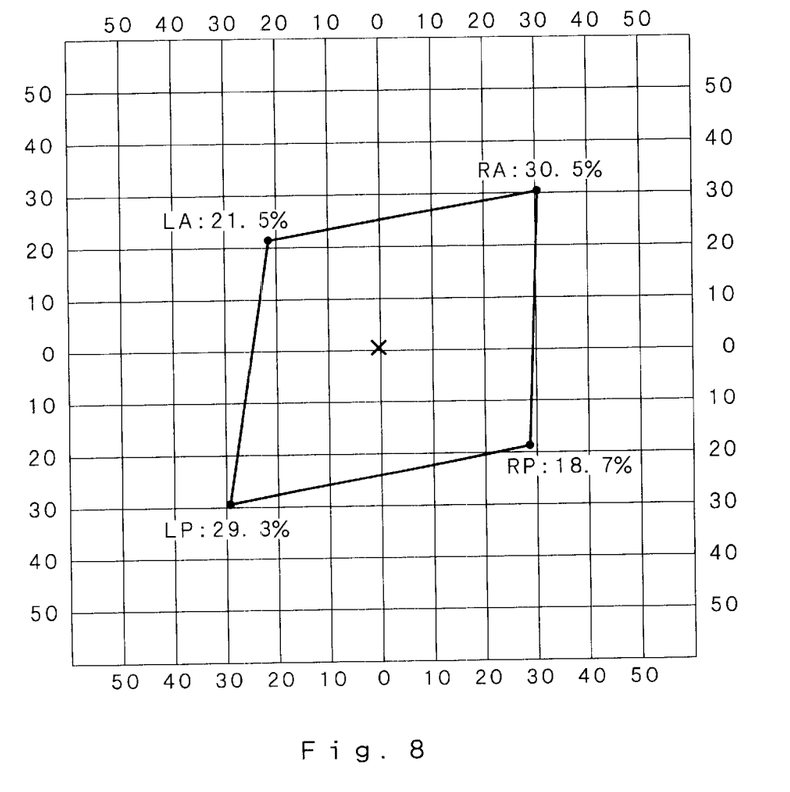
FIG. 8 is a graph showing mean values of four-divided weights of a patient's whole body before medical treatment.

FIGS. 6, 7 and 8 show averages of the OA, OP, IA, and IP distribution for 120 seconds rested on left foot and right foot, and those of whole body, and LA, LP, RA, and RP in FIG. 8 show the distribution of the weight rested on the front portion of left foot, the rear portion of left foot, the front portion of right foot, and rear portion of right foot respectively, and the marks x in those figures indicate the average position of the center of gravity rested on the left foot and the right foot, and that of whole body respectively.

Medical treatment applied the patient were mainly applying electrical current to loose portions such as muscle of the body to tighten the portion, applying acupuncture to loosen stiff portions of the body, and correcting the pulp horn of the backbone to improve balance and awake the person's nerve.

Figure 9:
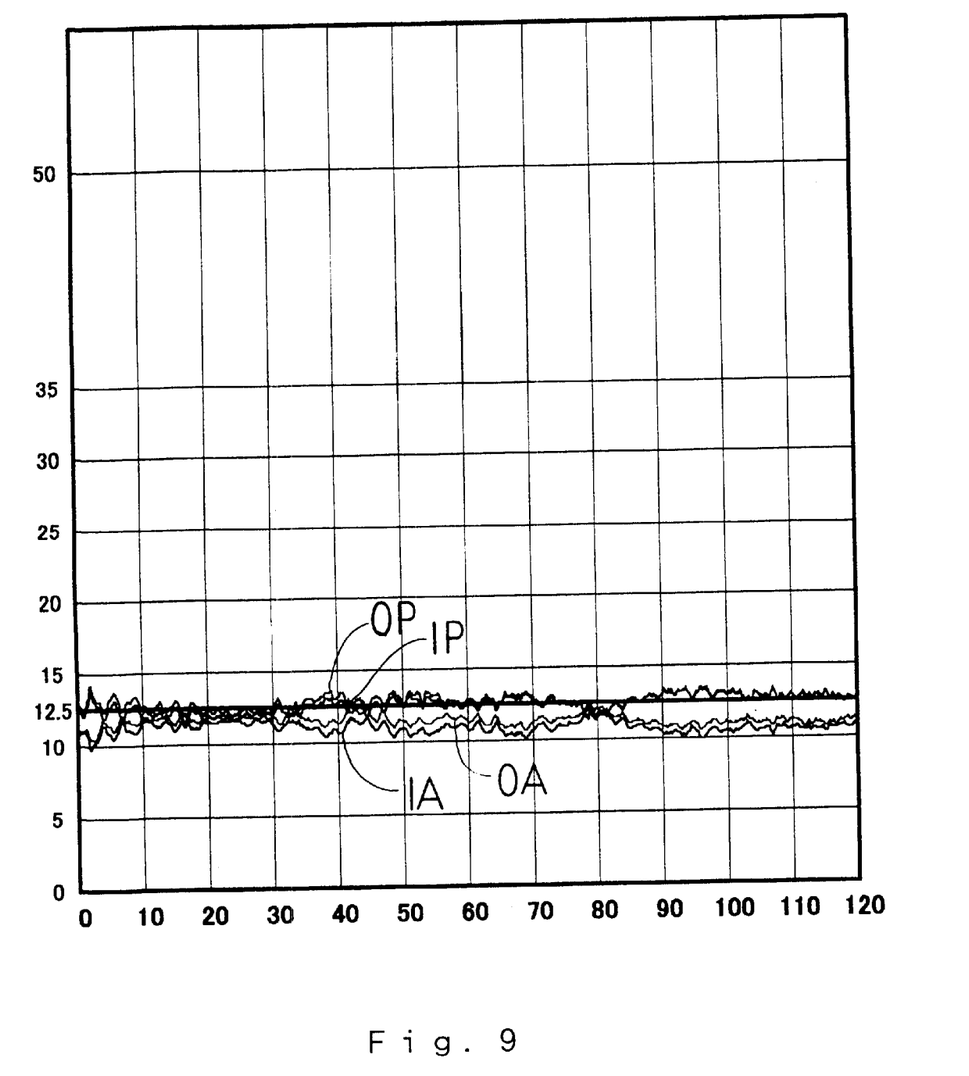
FIG. 9 is a graph showing four-divided weights of a patient rested on the left foot after medical treatment.
Figure 10:
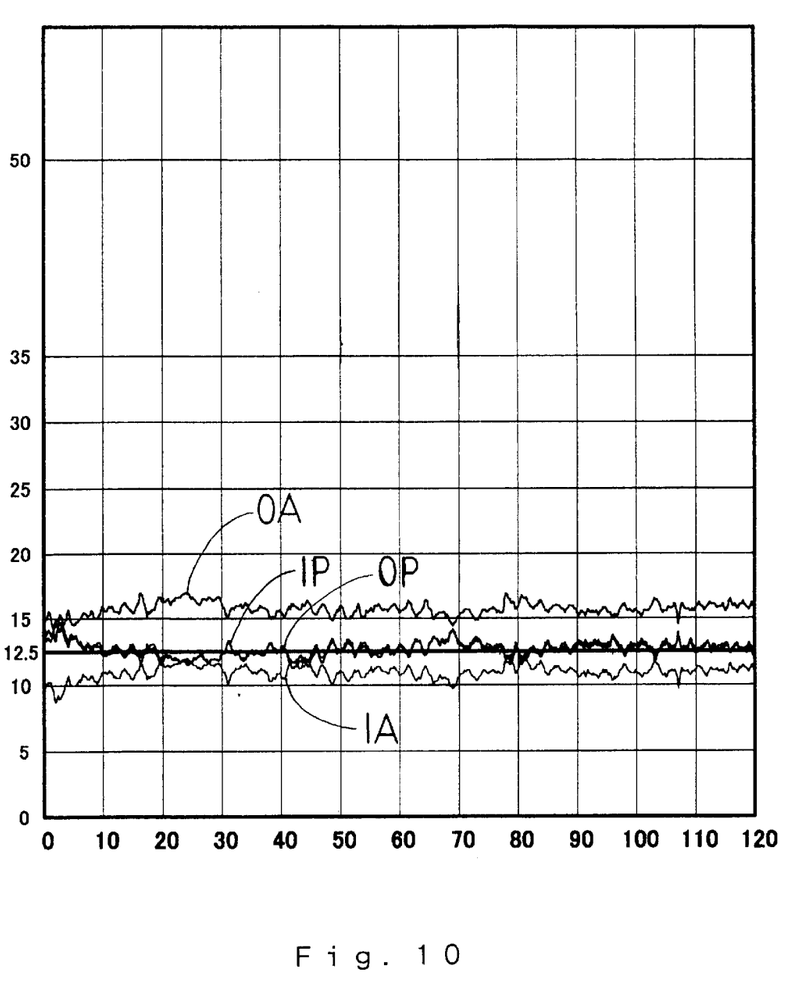
FIG. 10 is a graph showing four-divided weights of a patient rested on the right foot after medical treatment.
Figure 11:
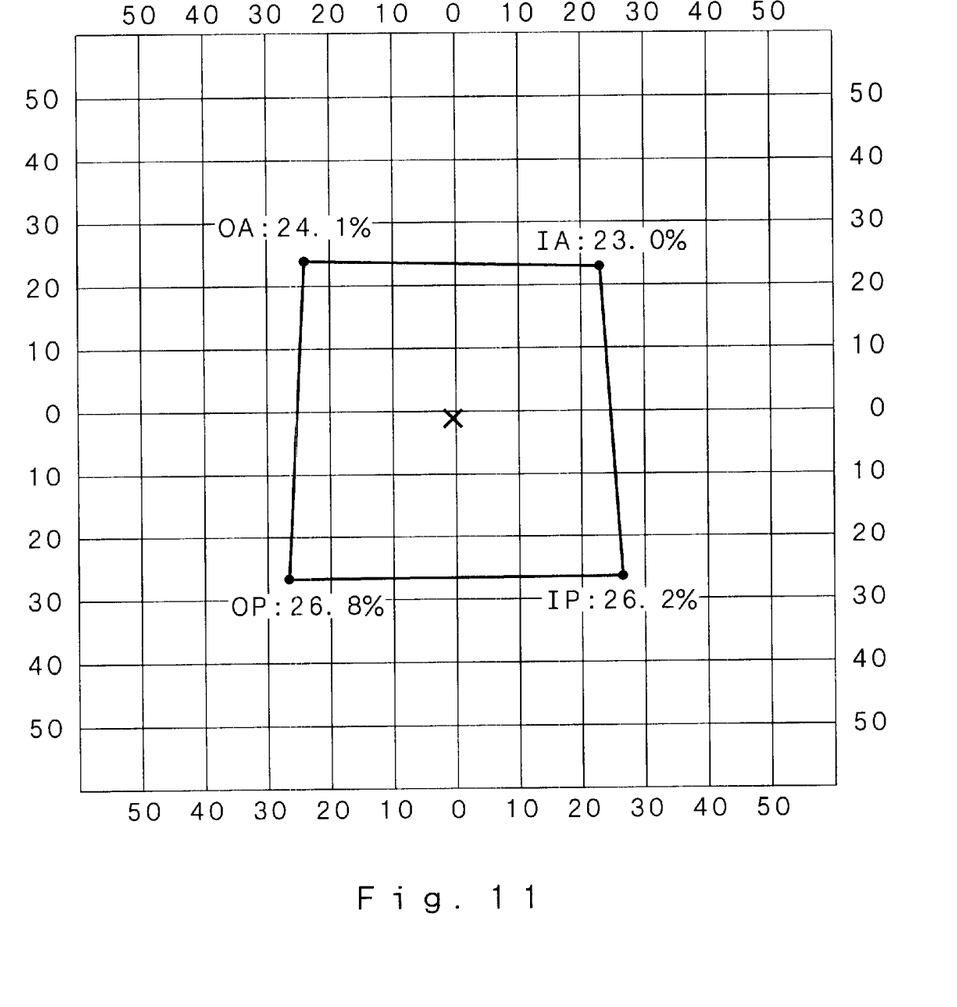
FIG. 11 is a graph showing mean values of four-divided weights of a patient rested on the left foot after medical treatment.
Figure 12:
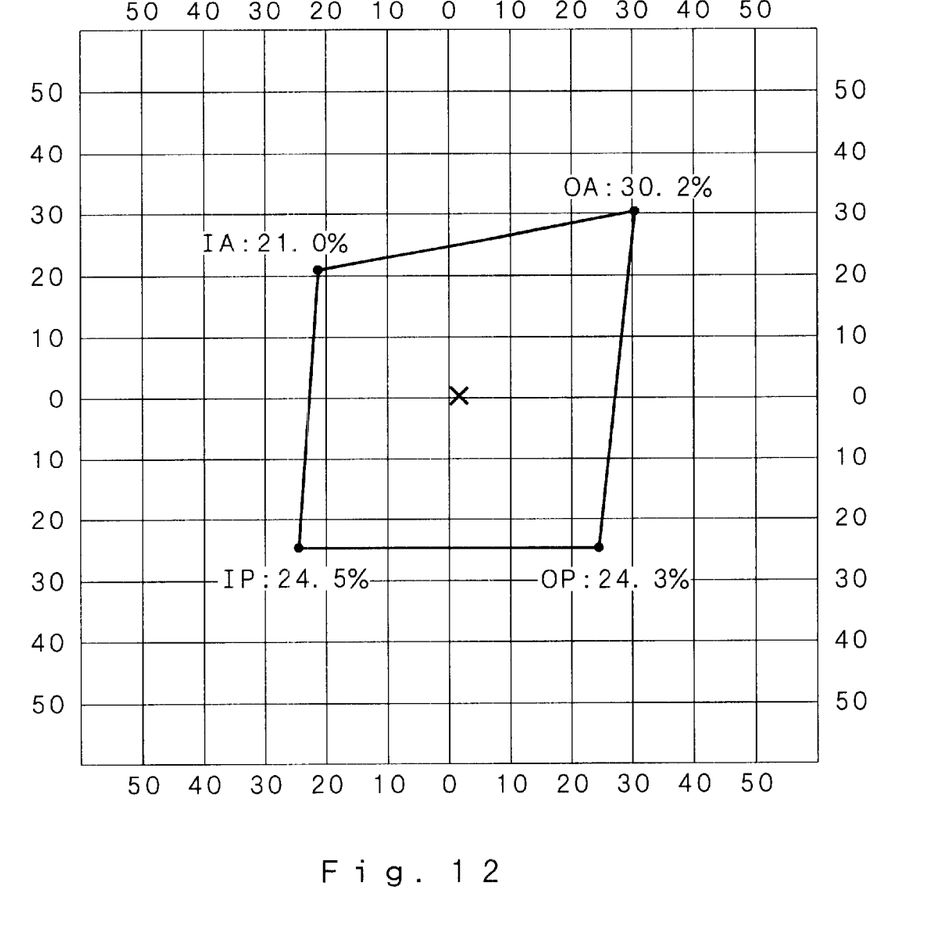
FIG. 12 is a graph showing mean values of four-divided weights of a patient rested on the right foot after medical treatment.
Figure 13:
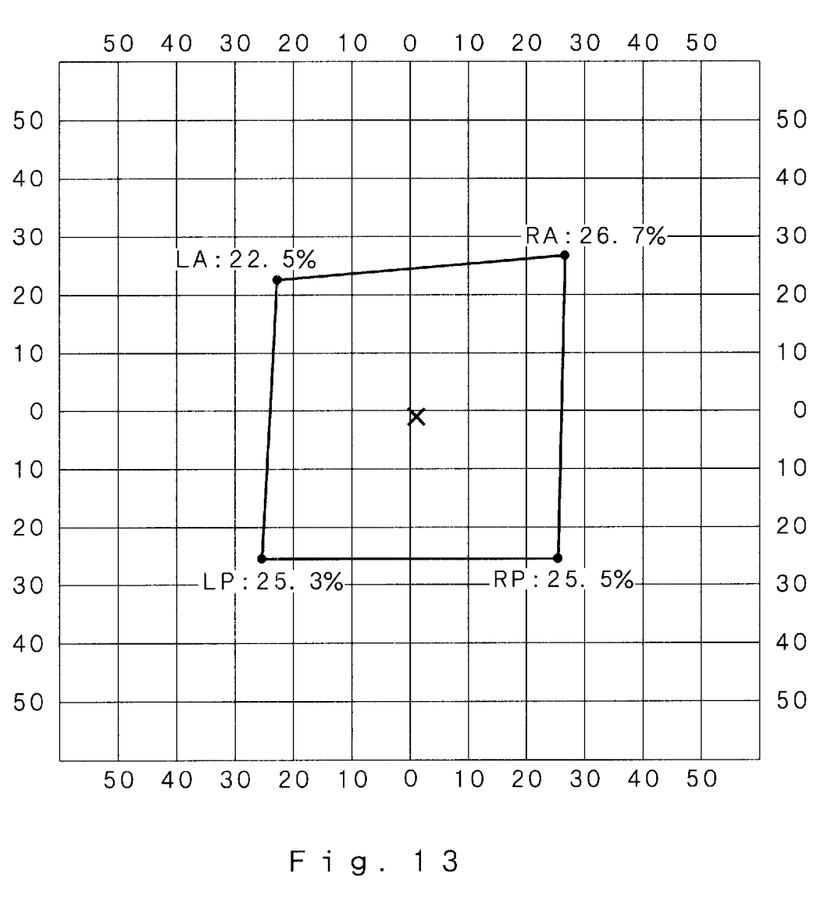
FIG. 13 is a graph showing mean values of four-divided weights of a patient's body after medical treatment.

The measurement results of the weight of the patient after the above-mentioned treatment are shown in FIGS. 9 to 13. FIGS. 9 and 10 correspond to FIGS. 4 and 5 before treatment. FIGS. 11, 12, and 13 correspond to FIGS. 6, 7, and 8 before treatment respectively.

Judging from FIGS. 4 and 5, and FIGS. 9 and 10, which show the transition of the weights rested on the left and right feet respectively, between the distributions before and after treatment, the fluctuation of the four-divided weights becomes smaller after treatment in comparison with before treatment, which means the balance of the patient is improved. Further, judging from FIGS. 6 to 8, and FIGS. 11 to 13, the balance of the averages of four-divided weights on the left foot and right foot, and those of the whole body are remarkably improved, the positions of the center of gravity of the weights approach the centers of the four-divided weights, which clearly shows the improvement of the weight balance.

In addition to the above data, it is effective for chiropractic and other medical treatment to use the OA, OP, IA, and IP distributions at predetermined intervals of time rested on left foot and right foot, and those of whole body, and the transition of the center gravity of the weights rested on the left and right feet, and those of the whole body.

What is claimed is:

1. A weighing machine comprising two weighing devices arranged right and left with a predetermined distance between them, wherein each said weighing device further comprises a case body with a bottom plate, and four weighing surfaces arranged right and left, and back and forth, on the bottom plate.

2. The weighing machine as claimed in claim 1, comprising channels formed between side walls of said four weighing surfaces.

3. The weighing machine as claimed in claim 1, wherein each of said weighing surfaces comprises a respective weighing mechanism comprising a load cell, and a converter to convert electrical voltages measured by each said load cell to respective weight data, storing means for storing said respective weight data, processing means for processing said respective weight data stored in the storing means, and displaying means for displaying data processed by the processing means.

4. The weighing machine as claimed in claim 2, wherein each of said weighing surfaces comprises a respective weighing mechanism comprising a load cell, and a converter to convert electrical voltages measured by each said load cell to respective weight data, storing means for storing said respective weight data, processing means for processing said respective weight data stored in the storing means, and displaying means for displaying data processed by the processing means.

5. The weighing machine as claimed in claim 1, comprising means for positioning a person to be measured on the two weighing devices.

6. The weighing machine as claimed in claim 1, wherein each of the four weighing surfaces comprises a respective weighing mechanism.

7. The weighing machine as claimed in claim 1, wherein the weighing surfaces are generally co-planar.

8. The weighing machine as claimed in claim 1, wherein the weighing surfaces comprise four rectangles having unequal lengths, in pairs.

9. The weighing machine as claimed in claim 1, wherein the weighing surfaces are contiguous.

* * * * *